United States Patent [19]
Elbert et al.

[11] Patent Number: 4,980,292
[45] Date of Patent: * Dec. 25, 1990

[54] TABLET DISPENSING

[75] Inventors: Lawrence E. Elbert, Huntington Beach; William A. Stark, Costa Mesa, both of Calif.

[73] Assignee: Baxter International Inc., Deerfield, Ill.

[*] Notice: The portion of the term of this patent subsequent to Jul. 9, 2002 has been disclaimed.

[21] Appl. No.: 943,819

[22] Filed: Dec. 17, 1986

Related U.S. Application Data

[63] Continuation of Ser. No. 656,755, Oct. 1, 1984, abandoned.

[51] Int. Cl.⁵ .......................... C12M 1/36; C12M 1/34
[52] U.S. Cl. ..................................... 435/289; 435/291; 422/63; 422/64; 422/65; 422/67; 422/99; 422/100; 422/102; 221/2; 221/3; 221/5; 221/7; 250/576
[58] Field of Search .................. 435/289, 291; 422/62, 422/64, 65, 67, 99, 100, 102; 221/2, 3, 5, 7; 250/576

[56] References Cited

U.S. PATENT DOCUMENTS

| | | | |
|---|---|---|---|
| 3,665,980 | 5/1972 | Croslin et al. | 422/67 X |
| 4,101,383 | 7/1978 | Wyatt et al. | 435/291 X |
| 4,130,394 | 12/1978 | Negersmith | 422/100 X |
| 4,276,383 | 6/1981 | Leighton et al. | 435/291 |
| 4,395,397 | 7/1983 | Shapiro | 435/291 X |
| 4,405,060 | 9/1983 | Hsei | 221/178 X |
| 4,420,566 | 12/1983 | Jessop et al. | 422/63 X |
| 4,451,433 | 5/1984 | Yamashita et al. | 422/100 X |
| 4,528,159 | 7/1985 | Liston | 422/102 X |

FOREIGN PATENT DOCUMENTS

| | | | |
|---|---|---|---|
| 56-76050 | 6/1981 | Japan | 422/63 |
| 58-95262 | 6/1983 | Japan | 422/64 |
| 2047401 | 11/1980 | United Kingdom | 435/291 |

OTHER PUBLICATIONS

Product Brochure: "This is Paramax, The Paramax Analytical System", American Dade, Division of American Hospital Supply Corporation, Miami, Fla., distributed by American Scientific Products, Division of American Hospital Supply Corporation, McGraw Park, Ill., published before Jun. 20, 1983, 12 pages.

Primary Examiner—Christine Nucker
Attorney, Agent, or Firm—Marjorie D. Hunter; Michael Bucklo

[57] ABSTRACT

A unique method and apparatus for dispensing tablets having particular application in the clinical analysis of biological samples. A series of containers are advanced past a plurality of processing stations, one of which is a table dispenser in turn. The processing stations are selectively activated by a controller. A sensor is associated with the tablet dispenser and is arranged to detect whether a tablet has actually entered a container. The sensor is activated only when the tablet dispenser is activated. The controller is responsive to the sensor in dependence upon the condition sensed by the sensor.

4 Claims, 4 Drawing Sheets

TABLET DISPENSING

This is a continuation of co-pending application Ser. No. 06/656,755 filed on Oct. 1, 1984 now abandoned.

BACKGROUND OF THE INVENTION

This invention relates generally to the dispensing of tablets, especially for use in the clinical analysis of biological samples. In particular, the invention relates to apparatus for dispensing tablets and to clinical analysis systems for the analysis of biological samples incorporating such apparatus. It also relates to methods of tablet dispensing and methods of clinical analysis employing tablet dispensing.

The present invention is particularly useful in automated clinical analyzers for determining the presence and levels of one or more selected constituents in relatively small biological liquid samples. Numerous automated clinical analyzers are known and widely used in hospital clinical laboratories. A preferred form of such analyzers is known as a single track clinical analyzer in which a series of cuvettes is advanced in turn past a plurality of processing stations arranged in line and the processing stations are selectively activated in varying permutations for different cuvettes.

An automated single track clinical analyzer is described in commonly owned U.S. Pat. No. 4,528,159, issued July 9, 1985 entitled "Automated Analysis Instrument System." The single track analyzer can perform different analytical profiles (i.e., profile analysis) or the same analytical test on a series of different patient samples (i.e., batch analysis). In either mode of the single track analyzer, the cuvettes containing samples are processed serially along a single track within the analyzer.

The single track analyzer is capable of performing multiple selected tests on a single specimen and is adapted for handling "stat" testing of emergency samples and routine chemistries. To this end the analyzer is adapted to dispense different permutations of reagent and liquid biological samples into successive, relatively small cuvettes advanced therethrough. The analyzer has multiple analysis stations to which the cuvettes are fed in turn so that examination of the treated samples can be effected at varying time intervals without limiting the throughput of the instrument. These multiple analysis stations permit their positioning at read times that are closely related to theoretical optimal kinetic and endpoint reaction read times.

The single track analyzer utilizes a disposable cuvette belt formed from thin plastic film and defining a series of discrete reaction compartments (cuvettes) which are transported in line through the instrument. The cuvettes are relatively small. They are generally, for example, capable of holding a final reaction volume of approximately 300 microliters. The patient sample in the cuvette is approximately 2 to 20 microliters. Such a cuvette belt is described in commonly owned U.S. patent application Ser. No. 284,842, filed July 20, 1981, entitled "Cuvette System For Automated Chemical Analyzers". Such a belt provides handling flexibility and avoids the crosscontamination associated with flow-through cuvettes as well as avoiding the washing required of reusable cuvettes.

The earlier clinical analyzers discussed above employed liquid reagent, and mixing of the reagent with the diluent prior to addition of the biological sample was achieved by pipetting a stream of the liquid reagent into the cuvette so as to produce a vortex-type mixing process. A preferred feature of the analyzer disclosed in U.S. Pat. No. 4,528,159 is that it is adapted to utilize dry particulate reagents, preferably in tablet form, which are dispensed into the cuvettes from a rotating carousel which can hold a large number of doses. A preferred embodiment of tablet dispenser is described in commonly owned U.S. Pat. No. 4,405,060 entitled "Tablet Dispensing Device".

In order to effect dissolution of the dry particulate reagent within the diluent prior to addition of the biological sample, the reagent and diluent are mixed by ultrasonic means. As disclosed in commonly owned U.S. patent application Ser. No. 575,924, filed Feb. 1, 1984, entitled "Clinical Analysis Systems and Methods", improved reliability and controllability of the analysis of the samples is achieved by again mixing the contents of the cuvette after addition of the sample by directing an air jet to an acute angle against the surface of the liquid in the cuvette. Particularly good mixing is obtained where the air jet is directed at the liquid surface adjacent its junction with the wall of the cuvette, the optimum point of contact of the air jet with the liquid surface being at the meniscus formed at the junction between the liquid surface and the wall of the cuvette.

A further advantageous feature of such an automated clinical analyzer is the use of microprocessor control, particularly for the dispensing and analysis station and the loading and transfer assembly for presenting to the analyzer containers having the samples to be tested.

A particular embodiment of the automated single track clinical analyzer according to aforesaid U.S. Pat. No. 4,528,159 is the subject of the Paramax Analytical System manufactured by American Dade, a division of American Hospital Supply Corporation, of Miami, Fla. "Paramax" is a registered trademark of American Hospital Supply Corporation. In this system, which is under microprocessor control, a cuvette belt is cut into sections, comprising one or several cuvettes, which are fed in turn past a reagent tablet dispenser, a diluent dispenser, an ultrasonic horn for mixing the reagent and diluent, a sample dispenser and eight photo-optical analyzer stations. During their passage through dispensing and analysis, the cuvettes are supported in a water bath kept at a constant temperature. After analysis, the cuvettes pass through a sealing station and into a disposal station.

Reagent tablets are dispensed from a rotary carousel and the biological liquids to be sampled are delivered in tubes to the sample dispenser one at a time by a carousel having priority access positions to allow immediate "stat" sample entry. Codes on the tubes identify the samples and a code-reader alerts the microprocessor to operate the analyzer in accordance with the coded information. A further reagent dispenser is arranged between two of the analyzer stations for producing further sample reaction to permit additional analysis.

SUMMARY OF THE INVENTION

The present invention provides an improved clinical analysis system for analyzing biological samples of the kind, as set forth above, including a plurality of processing stations, means for advancing cuvettes past the processing stations in turn and control means for selectively activating the processing stations with respect to the cuvettes whereby different cuvettes are differently processed. Where such a system includes a tablet dispensing means, it may occur sometimes that a tablet is not correctly dispensed, for example because the dispensing means fails or the tablet misses the intended cuvette, with the result that an incorrect analysis will be obtained.

In order to alleviate this problem, the analysis system according to the present invention includes sensing means arranged to sense whether a tablet has entered a cuvette aligned with the dispensing means. The sensing means is activated only when the tablet dispensing means is activated and the system control means is responsive to the sensing means in dependence upon the condition sensed by the sensing means.

Such an arrangement has several advantages. The sensing means is arranged to sense whether a tablet has actually entered a cuvette rather than merely sensing that a tablet has been dispensed where the tablet could still fail to enter the cuvette. The sensing means is only activated when the tablet dispensing means is activated which obviates the risk of indicating a failure in cases when no tablet should be dispensed. Further, by making the control means responsive to the condition sensed by the sensing means, effective action can be taken to avoid a faulty analysis being produced by the system.

The control means may be programmed to respond to the sensing means in various ways. Thus, it may merely inhibit further processing of the respective cuvette. However, it is preferred that the system rectify the fault either by reactivating the dispensing means or by processing another cuvette in place thereof. Where the sensing means indicates repeated failure of the tablet dispensing means, for example where it detects two successive failures, the controller may shut down the system for correction of the fault. The error may be reported to the operator and the particular cuvette having the error is flagged in the results printout or the particular test.

During processing, the cuvettes may be partially immersed in liquid to maintain a constant processing temperature. Further, a liquid may be dispensed into selected cuvettes before they reach the tablet dispensing means. Thus, a cuvette aligned with the tablet dispensing means may have liquid in it or surrounding it up to a predetermined level. In accordance with a preferred feature of the invention, the sensor is arranged at a level below the mouth of a cuvette aligned with the dispensing means but above the liquid level.

One embodiment of tablet dispenser according to the invention includes a motor for driving the dispenser to dispense a tablet and the sensor is only active when the motor is switched on and in operation, or for a timed interval after the motor is switched on. The sensor may have two light sources and a single detector.

An audio and/or visual warning signal may be generated to indicate to an operator the mis-dispensing of a tablet and/or the shut-down of the machine.

A method of analyzing biological samples is also provided in accordance with the invention in which cuvettes are advanced past a plurality of processing stations in turn and the processing stations are selectively activated with respect to the cuvettes so that different cuvettes are differently processed. One of the processing stations is a tablet dispensing means and the improvement comprises sensing whether a tablet has entered a respective cuvette aligned with the tablet dispensing means only each time the latter is activated and controlling subsequent activation of the processing stations in dependence whether the entry of a tablet into a cuvette has been sensed.

While particularly adapted for use in the clinical analysis of biological samples, the present invention has wider application to the selective dispensing of tablets in general. Thus, from another aspect, the invention provides improved apparatus for dispensing tablets into selected containers advanced therepast which comprises a tablet dispenser and control means for activating the tablet dispenser to dispense a tablet. Sensing means is arranged to sense whether a tablet has entered a container. The sensing means is activated only when the tablet dispenser is activated and the control means is responsive to the sensing means in dependence upon the condition sensed by the sensing means.

In accordance with another feature of the invention, tablets are dispensed into selected containers advanced past a tablet dispenser by a method including the steps of (a) advancing containers in turn past the tablet dispenser, (b) selectively activating the tablet dispenser, (c) sensing whether a tablet has entered a container only each time the tablet dispenser is activated, and (d) controlling subsequent step (a) and/or step (b) in dependence whether the entry of a tablet into a container has been sensed.

DESCRIPTION OF THE DRAWINGS

Other features and advantages of the present invention will become apparent from the following description taken in conjunction with the accompanying drawings wherein:

FIG. 6 is another block diagram including a partial schematic illustrating the dispensing and control system in greater detail.

DETAILED DESCRIPTION

Figure 1:
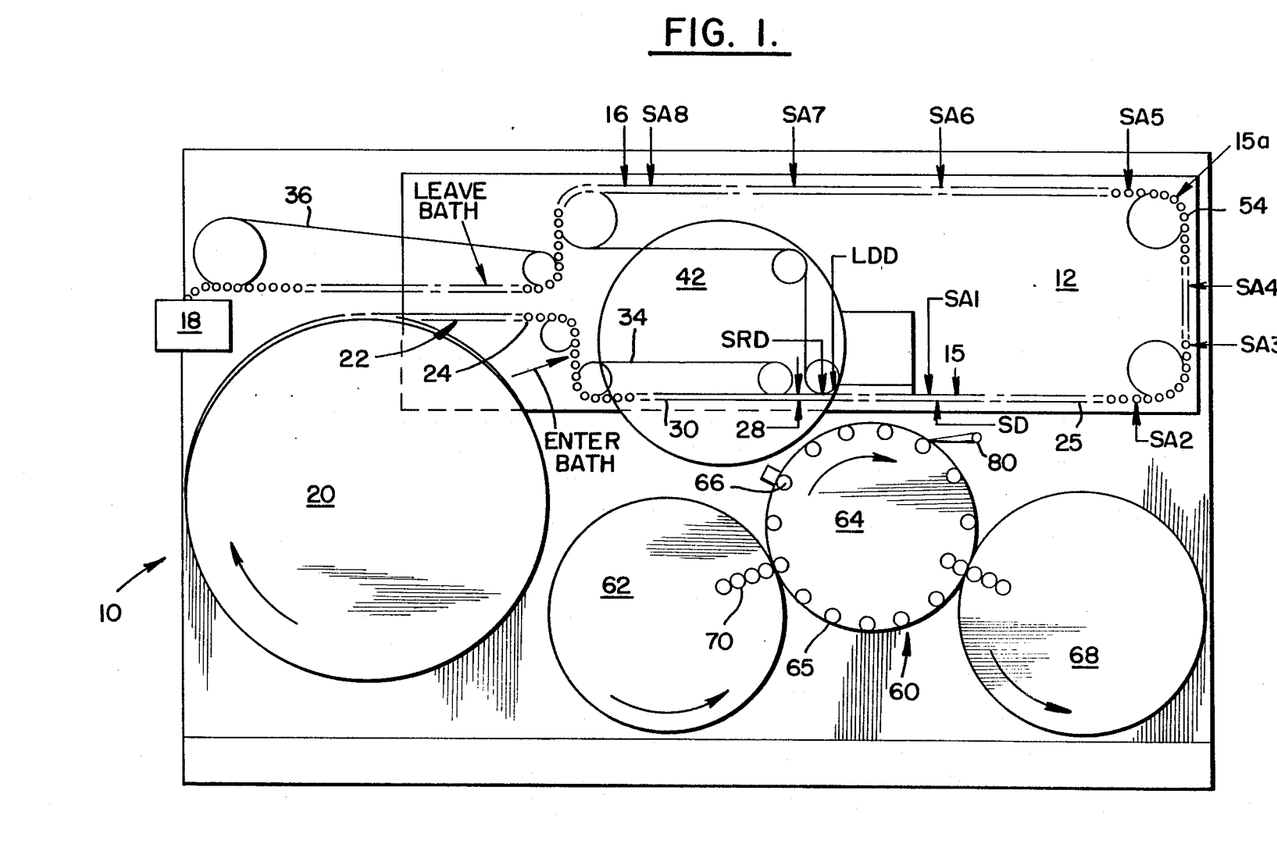
FIG. 1 is a schematic plan view of an automated clinical anlyzer according to the present invention.
Figure 2:
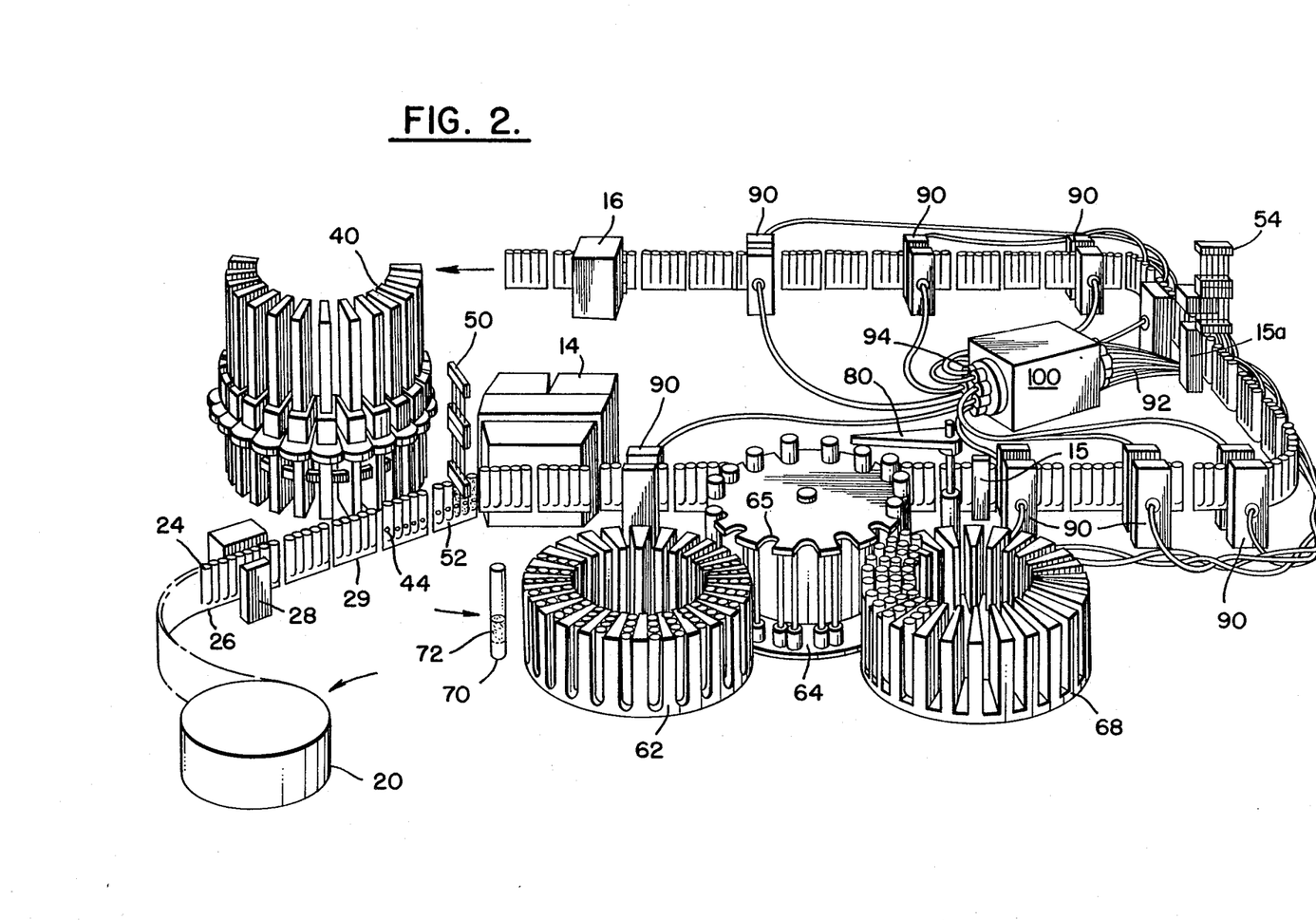
FIG. 2 is a partial perspective view of the automated clinical analyzer shown in FIG. 1.

FIGS. 1 and 2 illustrate an automated clinical analyzer 10 generally as described in the aforesaid U.S. patent application Ser. No. 575,924. More particularly, the analyzer is a modified Paramax Analytical System as manufactured by American Hospital Supply Corporation. The analyzer 10 is adapted for the testing of constitutents in biological fluids, such as blood samples, urine, etc.

Figure 5:
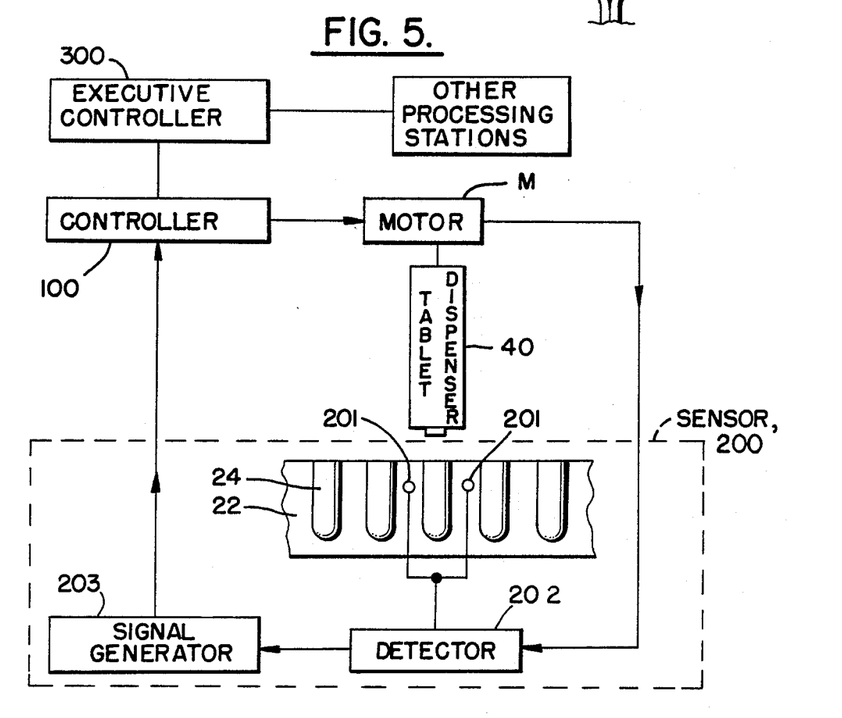
FIG. 5 is a block diagram illustrating schematically the control system of the analyzer.

The analyzer comprises a series of processing stations past which strips of disposable reaction cuvettes are indexed or advanced. The cuvettes 24 are supplied from a supply reel 20 as a continuous cuvette belt 22 and are indexed through the analyzer by tractor conveyor 30 which engages a row of index holes in the cuvette belt. The cuvettes are indexed in turn past the following processing stations: a belt cutter 28 for dividing the belt into sections; a tabletted reagent dispenser 40; a diluent and liquid reagent dispenser 50; an ultrasonic mixing horn 14; a sample dispenser 80 for dispensing biological samples delivered by a transfer carousel 64; an air-jet mixing apparatus 15 for mixing the sample with the reagent and diluent in the cuvettes; eight photometric read stations 90; a further reagent dispenser 54; a further air-jet mixing apparatus 15a for mixing the sample and the further reagent; a cuvette sealer 16 and a cuvette collection station 18. During their passage through the analyzer, the cuvettes are carried in a water bath 12 maintained at a constant temperature. An executive or main microprocessor 300 controls the overall operation of the analyzer (as schematically illustrated in FIG. 5). The processing stations and their functions will now be described in detail.

The disposable cuvettes 24 are conveniently packaged in reels of as many as 2100 cuvettes. The belt 22 defines entirely separate reaction vessels designed to eliminate cross-contamination of reaction mixtures. The cuvette belt 22 is preferably constructed and made in the manner more fully described in aforesaid U.S. patent application Ser. No. 284,842, as will now be described briefly with particular reference to FIGS. 4 and 5.

Figure 4:
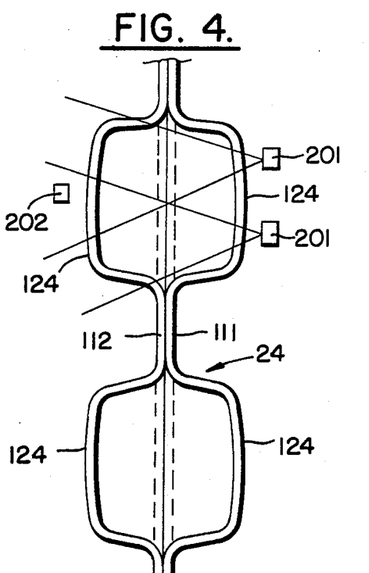
FIG. 4 is a plan view of the cuvette belt as shown in FIG. 3.

The belt 22 comprises two strips 111, 112 of transparent plastics material which are molded and sealed together to form a series of discrete, side-by-side parallel compartments (cuvettes) 24 separated by webs 115. The compartments are closed at one end and have an open mouth 117 at the other end so as to receive and retain fluid therein. For example, the cuvettes can be in the order of size so as to be capable of holding about 500 microliters of fluid.

The compartments or vessels 24 are substantially rectangular in cross-section, being elongated along the length of the belt. They have generally parallel side faces 124 which define optical windows providing an optical path of precise length through each cuvette for accurate examination of the samples at the read stations 90. The flat web material 115 between the vessels 24 includes a transport strip portion extending alongside the closed ends thereof which is formed with indexing perforations or hole 26. These perforations are engaged by the tractor conveyor 30 of the analyzer 10 for conveying the cuvettes therethrough and maintaining a precise alignment of the optical paths through the cuvettes with the photooptical examining system at the analysis stations 90.

The conveyor 30 comprises a single continuous guide and support track extending through the analyzer having a main tractor belt 32 which engages the indexing holes 26 in the cuvette belt 22 and advances the cuvettes through the instrument at a predetermined rate of advance under control of the executive microprocessor 300. A short loading belt 34 threads the cuvette belt 22 into engagement with the main tractor belt 32. The conveyor 30 advances or indexes the cuvettes through the analyzer 10 in steps corresponding to the spacing between cuvettes (the pitch of the belt) with the cuvettes being stopped and held stationary for a dwell period between each advance. Each step may suitably correspond to a time interval of 5 seconds with a 4 second dwell time between each indexing advance of the cuvettes.

The reagent tablet dispenser carousel 42 comprises a circular array of tabletted reagent dispensers 40 and can be rotated to bring the correct solid reagent dispenser to solid reagent dispensing point "SRD" to drop a single reagent tablet 44 into a cuvette 24. As illustrated, the carousel 42 accommodates thirty-two reagent tablet dispensers 40. It is rotated under control of slave microprocessor 302 to bring the correct tablet dispenser to the dispensing point for each cuvette. The dispensers 40 are detachable and can be loaded randomly. An automatic flagging system indicates when a dispenser is low in tablets.

As schematically illustrated in FIGS. 3–6 4, the tablet dispensers 40 are driven by a motor M for dispensing the tablets and, in accordance with the present invention, a sensor 200 disposed beneath the dispensing point "SRD" is arranged to sense whether a tablet actually enters the cuvette 24 aligned with the dispenser 40. The sensor 200 is connected through a feedback circuit (see FIGS. 5 and 6) to the executive microprocessor 300. This arrangement is described fully hereinbelow.

The diluent and/or liquid reagent dispenser 50 is located adjacent to carousel 42 for adding under the control of slave microprocessor 302 sufficient diluent 52 for reagent tablet 44 dissolution and/or for dispensing a liquid reagent into the reaction vessel (cuvette) 24 at point "LDD". The ultrasonic horn 14 acts on the cuvette contents for a sufficient length of time; for example, 45 seconds, to totally dissolve the reagent tablets.

A sample loading and transfer carousel assembly 60 is located downstream of the reagent and diluent dispensers. This carousel assembly, under the control of slave microprocessor 324, comprises a loading carousel 62 into which patient samples 70 are randomly loaded; a transfer carousel 64 which accepts the patient samples 70 from loading carousel 62, identifies the patient sample by means of a bar code reader 66 which reads a bar code label 72 placed on the patient sample container and coninuously feeds the patient samples into the system; and finally, an unloading carousel 68 receives the patient samples 70 after testing and stores them in an organized manner in the event that they must later be located and retrieved.

The loading carousel 62 permits continuous random loading of up to 96 patient samples. The transfer carousel 64 continuously feeds patient samples into the system for maximum throughput. Standard collection tubes or micro sample tubes may be accommodated thus allowing utilization of the same containers in which the sample was collected; for example, in the case of blood samples, the "Vacutainer" tube which is commonly used to draw the serum specimen.

Sampler 80 for dispensing samples into the cuvettes 24 at point "SD" is located adjacent to transfer carousel 64. This sample dispenser is designed to aspirate about 2 to 20 microliters of patient sample 70 from its container in the transfer carousel and dispense it into a cuvette 24 along with sufficient diluent to make up approximately 100 microliters during the four second dwell period while the cuvette is aligned with the sampler.

The air-jet mixing apparatus 15 (and 15a) direct an air jet at an acute angle against the liquid surface in the cuvette adjacent its junction with the cuvette wall to create a vortex thus producing a thorough mixing of the sample with the reagent and diluent. In a preferred embodiment, the apparatus has a fixed, inclined nozzle and the cuvettes 24 are aligned in position beneath the nozzle and the air jet is switched on only during the dwell period when the cuvette is stationary. In order to ensure that the air jet correctly strikes the liquid surface, the liquid level is closely controlled. The structure and operation of preferred embodiments of the air-jet mixing apparatus 15 and 15a are described in detail hereinafter.

Eight photometric analysis stations 90, which are controlled by slave microprocessor 310, are located at points "SA1" through "SA8" along the cuvette track 30. These analysis stations are connected by individual optical guides 92 and 94 to photo-optical system 100. The station "SA1" is arranged following the ultrasonic horn 14 for verifying proper reagent dispensing and dissolution. This photo-optical system 100 is described and illustrated in commonly owned U.S. patent application Ser. No. 284,841, filed July 20, 1981, entitled "Multichannel Spectrophotometer".

The second reagent dispenser 54 permits further reaction of the sample to be obtained following initial testing and is shown arranged between analysis stations "SA4" and "SA5". It could be located between any of the analysis stations "SA2" to "SA8". This capacity for optional reagent additions or triggered reaction capability gives added analytical versatility for multiple reagent test situations.

The further air-jet mixing apparatus 15a according to the invention provides for thorough remixing of the cuvette contents following addition of further reagent at dispenser 54.

The cuvette sealer 16 seals the tops of the tested cuvettes for convenient clean disposal of completed samples at the cuvette disposal location where they are neatly collected into a lined disposal bin.

The executive microprocessor control system 300 of the clinical analyzer, which suitably has a Z80 processing unit, controls in an overall manner all the operating units thereof in accordance with sample and test information inputted at a suitable operator interface keyboard. In accordance with the desired test results, quantities of a single sample may be dispensed into one or more cuvettes either alone or in combination with any one or more of the solid and liquid reagents and diluent and examined at any one or more of the analysis stations 90. Test results are displayed on a screen and can be printed out.

Normal operation of the instrument system will now be described in detail. A phlebotomist draws a patient blood sample 70 which is positively identified by a bar code label 72 placed on the container in which the sample is drawn. After centrifuging the sample to separate the serum, the sample along with as many others as desired is placed in loading carousel 62 which is then placed into the instrument loading and transfer carousel assembly 60. For emergency stat testing, the patient sample 70 may be loaded directly into one of the empty sample receiving slots 65 of transfer carousel 64, or may be exchanged with a sample container already loaded in transfer carousel 64 prior to bar code reader 66.

The loading carousel is then automatically indexed to a position where the patient sample 70 is transferred into an empty sample receiving slot 65 of transfer carousel 64. The transfer carousel 64 then is indexed around to bar code reader 66 which identifies the patient sample. This sample identity is fed to the external data management console 340, which is in operative relationship with executive controller 300, for a scheduled test(s) to be run for this sample that has already been entered into the console 340 by the laboratory technician.

The executive microprocessor 300 then begins the advance of the cuvette supply reel 20 and belt 22 into cuvette conveyor 30 in response to this sample identification. This cuvette supply advance is accomplished by the loading belt 34 which threads the cuvette belt into main tractor belt 32. If bar code reader 66 detects that there are no further samples to be tested, the executive microprocessor 300 will activate cuvette belt cutter 28 which divides cuvette belt 22 into sections 29 having a number of cuvettes corresponding to the number of analysis reactions to be performed at a given time. This procedure minimizes waste for single tests or stat situations. In addition, the cuvette belt cutter 28 may also be periodically operated during continuous operation of the instrument in order to prevent the length of the cuvette belt (which must be disposed of) from becoming unmanageable.

As it is fed into the instrument, the cuvette belt 22 enters a water bath 12 which will maintain the reagent and sample reaction mixture at a predetermined incubation temperature. This reaction temperature is generally either 30 degrees C. or 37 degrees C.

For the sake of simplicity, it should also be noted that in FIG. 1 each circular cuvette position point 25 along cuvette track 30 represents a 5 second period. In other words, every 5 seconds the control microprocessor will step a particular cuvette reaction compartment 24 to the next circular position along the cuvette track 30.

During the time that the transfer carousel 64 is indexing the sample 70 between the bar code reader 66 and its position where sample dispenser 80 aspirates a portion thereof, an appropriate reagent is added at either point "SRD" or "LDD" to the reaction compartment that is timed by the executive controller 300 to receive the sample. The executive controller 300, in cooperation with slave controller 302, causes the proper reagent to be dispensed from one of the thirty-two different tabletted reagent dispensers 40 that can be accommodated by dispenser carousel 42, or, in cooperation with slave controller 306, causes the multiple liquid reagents that can be accomodated by diluent/liquid reagent dispenser 50, in response to the patient sample identification by bar code reader 66.

If a tabletted reagent is dispensed, sufficient diluent for tablet dissolution is added thereto at point "LDD" and an ultrasonic horn 14 is utilized to provide 45 seconds of high energy ultrasound to completely break up and dissolve the reagent tablet. In the preferred embodiment, this reagent mixture has a volume of about 200 microliters.

After this reconstitution of the reagent in the predetermined amount of diluent, the reaction compartment is passed to a reagent quality control analysis station at point "SA1". Here, each reagent mixture may be photometrically analyzed to verify proper reagent dispensing and dissolution. Furthermore, the executive controller 300 can also utilize this reading to adjust for any minor variation in reagent amount and resulting concentration that may exist from tablet to tablet.

Next, the reaction compartment 24 is transported to point "SD" where dispenser 80 will dispense the appropriate patient sample into the reaction compartment 24. As noted above, the main transport belt 32 of cuvette conveyor 30 is carefully synchronized with the reagent dispensers and the sample to insure that the proper reaction mixture is obtained as ordered by the executive controller 300. Since sampler 80 is the only non-discrete element of the analysis system, its probe is flushed with additional diluent to prevent contamination and carryover between samples. In the preferred embodiment, the final reaction volume is about 300 microliters. Following addition of the sample, the contents of the cuvettes are thoroughly mixed at air-jet mixing station 15.

It has been found desirable to dispense an amount of each patient sample into a reaction compartment without a reagent being added to obtain a sample blank. This sample blank value may be obtained at any or all of the last seven analysis stations as required.

The second reagent dispenser 54 is located further down the track of cuvette conveyor 30 for multiple or triggered reaction capability. For example, such a reagent dispenser would be useful in conducting CKMB constituent analyses. The further air-jet mixing station 15a provides thorough mixing of the cuvette contents following this addition.

At the end of the cuvette conveyor 30, the cuvette sealer 16 is located to seal the tops of the cuvette reaction compartments after testing for convenient and sanitary disposal of the samples. After passing through the cuvette sealer 16, the cuvette belt 22 is stripped off of the main transport belt 32 by an unloading belt 36 which removes the tested cuvettes from the water bath 12 and automatically discards them into a disposal bin at cuvette collection station 18.

The solid reagent or tablet dispenser 40 utilized herein is described in detail in the aforementioned U.S. Pat. No. 4,405,060. The reagent tablets are held in a tablet dispenser having an upper portion adapted for storing a relatively large number of tablets and a lower base with a dispensing orifice in its bottom. The dispenser carousel 42 in cooperation with executive controller 300 and slave controller 40 rotates the correct tablet dispenser to the dispensing point over the cuvette and dispenses a tablet into the cuvette.

Assuming the correct dispenser is aligned with the cuvette, the sensing and control system unique to the present invention will now be described in detail with reference to FIGS. 3 to 6. As mentioned above, the dispensers 40 are driven by a motor M for dispensing the tablets one at a time, the motor being automatically engaged with the dispenser 40 that is aligned with the dispensing point "SRD". The motor M is activated by a signal from the slave microprocessor 302 so as to cycle the dispenser to dispense a single tablet into the cuvette aligned therewith.

Figure 3:
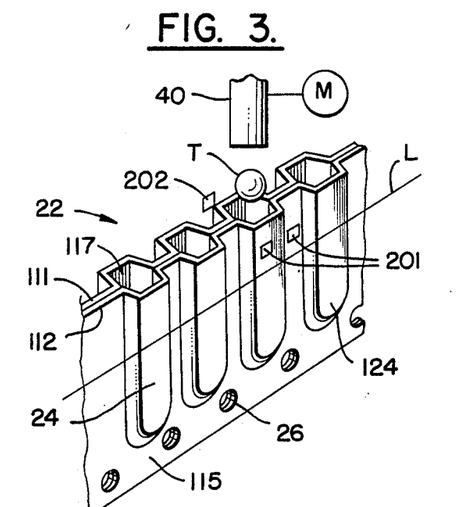
FIG. 3 is a perspective view of a cuvette belt showing one of the cuvettes aligned with the tablet dispenser.

In accordance with the invention, the detector 202 is arranged at the dispensing point "SRD" so that it will sense whether a tablet T has actually entered the cuvette. To this end, the sensor is arranged below the level of the mouth of the cuvette and includes light sources 201 at one side of the cuvette, which project light through the optically clear side faces 124 of the cuvette, and a detector 202 arranged at the opposite side of the cuvette.

In the embodiment illustrated, due to the elongated dimension of the cuvettes along the length of the belt, two side-by-side light sources are provided to give an adequate spread of light across the entire field of view through the cuvette. A single detector 202 will normally be sufficient to detect a change in light level caused by the passage of a tablet. Thus, two light emitting diodes (LEDs) 201 may be used in conjuction with a single phototransistor detector 202. It will be remembered that the cuvettes are partially immersed in water bath 12 to control the analysis temperature during processing so that they are surrounded by liquid up to a predetermined level L (FIG. 3). In order to provide optimum optical conditions for the detector 202, it is arranged above the water level L.

The detector 202 is connected to the slave microprocessor 302 control unit through a feedback circuit, as shown in FIGS. 5 and 6, which includes a signal generator 203 which generates a signal indicative of the condition sensed by the detector 202; i.e., whether or not a tablet has interrupted the light beam and thus entered the cuvette. This signal is transmitted from slave controller 302 to executive controller 300. As explained below, the executive microprocessor 300 controls subsequent operation of the analyzer in dependence upon the condition ("dispense completed" or "dispense failed") sensed by the sensor.

Thus, on receipt of a "dispense failed" signal indicating that a tablet has failed to enter the cuvette, the executive controller 300 will vary the normal or preset operation of the analyzer which has been described above. It will be understood from the foregoing that tablets will be dispensed only into selected cuvettes, ie less than all of said cuvettes and in order to avoid the production of spurious "dispense failed" signals when no tablet might have been dispensed, the sensor 200 is operatively linked to the motor M so as to be activated only when the motor M is activated to dispense a tablet. The sensor may be adapted to operate only while the motor is switched on or for a fixed time after the motor is switched on. Thus a signal indicating the absence of a tablet can only be generated when the motor M of the tablet dispenser 40 is activated. Also, the operation of conveyor 30 is not dependent upon the dispensing of a tablet by the dispenser 40. It will be understood that while the signal generator desirably produces a positive "dispense failed" signal, it may only produce a signal indicating when a tablet is successfully dispensed ("dispense completed"), the slave microprocessor 302 being programmed to recognize that the lack of a signal within a predetermined time after activation of the motor M indicates "dispense failed".

On receipt of a "dispense failed" warning, the executive controller 300 may respond in various ways. For example, it may delay advance of the cuvette belt and activation of the other processing stations for a further "dwell" period while reactivating the tablet dispenser with the same cuvette aligned with it. Or, it may inhibit further processing of the respective cuvette in which case it will preferably process a subsequent cuvette in place thereof. Where the detector 202 indicates repeated failure of the tablet dispenser 40; for example, where it detects two successive failures, the executive controller 300 may shut down the system for correction of the fault. An audio and/or visual warning signal may be generated to indicate to an operator the non-dispensing of a tablet and/or the shut-down of the system.

By way of example, one processing cycle of the analyzer will now be described to illustrate how its operation may be varied upon failure of the tablet dispenser. It will be assumed for the sake of brevity that the processing cycle involves only three cuvettes although it will be understood that such a cycle will normally involve a greater number of cuvettes.

It is assumed also that the executive controller 300 has been programmed to process the cuvettes as follows. The first cuvette is to receive a reagent tablet from the tablet dispenser 40, diluent from liquid dispenser 50, mixing by horn 14, a liquid biological sample from dispenser 80 and mixing by air-jet mixer 15, the reaction product being read at photometric read stations SA1, SA2, SA4 and SA6. The second cuvette is to receive liquid reagent from dispenser 50, the same biological sample from dispenser 80, mixing by air-jet mixer 15, further reagent from dispenser 54 and further mixing by air-jet mixture 15a, the reaction products being read at photometric read stations SA1, SA2 and SA5. The third cuvette is to be processed identically to the first cuvette but receiving a different biological sample.

The cuvette belt 22 is advanced under control of the executive controller 300 to the tablet dispensing point "SRD". The solid reagent carousel has been rotated by slave controller 302 under the general direction of executive controller 300 to place the correct reagent cartridge over the cuvette. The slave controller 302 activates the motor M which in turn activates the sensor 200. Assuming that the dispenser works successfully and the tablet is dispensed into the first cuvette (cuvette "1"), the sensor beam will be interrupted and a "dispense completed" signal transmitted to the slave controller 302 by the signal generator 203. The executive controller 300 will now proceed in accordance with its preset program to advance the cuvette belt one step so that the second cuvette will be aligned with the tablet dispenser 40 at point SRD. Cuvette "1" will be between stations during this time. Cuvette "2" is not intended to receive a tablet and the motor M and thus the sensor 200 will not be activated. Thus, after the normal dwell period, the belt will be advanced one further step which will bring cuvette "1" up to the diluent dispensing point "LDD" and cuvette "3" to the tablet dispensing point "SRD". The executive controller 300 now activates the diluent dispenser 50 through slave controller 306 to dispense a measured amount of diluent into cuvette "1" and at the same time the executive controller 300 activates via slave controller 302 the motor M of tablet dispenser 40 which in turn activates the sensor 200.

For the sake of description, it is assumed that at this time the dispenser 40 jams and no tablet is dispensed in cuvette "3". Since, after a predetermined timed interval the light beam from the LEDs 201 will not have been interrupted, the signal generator will generate a "dispense failed" signal and transmit this to the slave controller 302 which passes the information on the failure back to executive controller 300. Executive controller 300 will flag the results held by it for cuvette "3" so that such results will be ignored as a valid test, and will record the fact of a dispense error.

In addition, the operator is informed, such as through a printout of printer 322, that a tablet drop error has occurred at the particular dispenser in the carousel. If the operator does nothing, the analyzer will continue to operate as usual. However, there is a "pause" button on the control panel 360 through which the operator can tell the executive controller 300 to interrupt the loading of new tests in the processing stream but continue with the processing of all those cuvette tests that had been begun. The executive controller 300 interrupts the loading of new tests, cuts the cuvette belt at a point upstream of the last cuvette selected for a test and places the solid reagent slave controller 302 into a manual mode so that the operator can manually replace the faulty cartridge. Then the operator pushes the start button on control panel 360 which informs the executive controller 300 to restart the feeding of the cuvettes to the solid reagent station "SRD", start loading new tests from the point it left off, and remove the solid reagent slave controller 302 from its manual mode. The "pause" mode selection, of course, can be done automatically in response to the detection of the "dispense failed" signal.

Instead of interrupting the advance of the cuvettes and repeating the dispensing step on the same cuvette, as described above, the microprocessor system may be programmed to repeat the tablet dispensing step on the next cuvette ("4") in line and treat this cuvette as the third cuvette during the remainder of the processing steps. According to this sequence, upon successive dispensing failures, the machine will shut down as described above the cuvette "4" will remain aligned with dispensing point "SRD" when the machine is restarted. It will be understood that this sequence may be less practical where tablet dispensing is not the first processing step.

FIG. 5 shows a schematic illustration of one embodiment of the control system for the analyzer. Any suitable control system, or elements thereof, can be used. For instance, the executive or main controller 300 may be a DEC "MICRO 11" computer system sold by DIGITAL Equipment Corporation, Maynard, Mass. It is tied by a suitable computer link to data management controller console 340. The executive controller 300 controls the overall system by communicating with various analyzer stations and the console 340 which runs calculations, programs, etc. In addition, executive controller 300 keeps track of test conditions, the overall timing and the system's state (run, stop, etc), and stores the readings from the analyzer tests. A systems status monitor 330 which reads voltages, performs diagnostics, checks various system status, etc., communicates to the executive controller 300 through its slave controller 328.

The slave controllers 302, 306, 310, 314, 316 and 324 can be 8741 microprocessors sold by Intel Corporation, Santa Clara, Calif. Slave controllers 320 and 328 can be 8742 and 8748 microprocessors, respectively, also sold by Intel Corporation. All of these processors are in the 8048 Intel family. The executive controller 300 can be a Z80, Zilog Processor sold by Exxon Corporation, NY, N.Y.

Key board 362, belt cutter 28, mixing stations 14, 15, 15a, cuvette drive and cuvette sealer 16, control panel 360 and alarm 364 are connected directly through a suitable I/O (Input/Output) interface 350 to controller 300. The tablet reagent dispenser 40, liquid reagent dispensers 50, 54, photometric read stations 90, printer 322, transfer carousel and bar code reader 64, 66 and systems status monitor 330 are tied into the executive computer 300 through their associated slave controllers 302, 306, 310, 320, 324, 328, respectively. Sample dispenser 80 uses two slave controllers 314, 316 to link it to the executive controller 300.

Although particular configurations and features of the present invention have been discussed in connection with the above-described preferred embodiments thereof, it should be understood that those skilled in the art may make various changes, modifications and substitutions thereto without departing from the spirit and scope of the invention as defined in the appended claims.

For example, although the system described above has only one tablet dispensing point "SRD", it is within the scope of this invention that two or more tablet dispensing locations be provided, each one having its own sensor and feedback to the slave and executive controllers.

In the embodiment of analyzer described herein, a tablet from dispenser 40 is loaded into an empty cuvette. However, the cuvette may have been previously charged with a liquid; e.g., diluent, so that the cuvette contains liquid to a predetermined level therein. This liquid may be present whether or not there is liquid surrounding the cuvette and may extend to a different level. For the same reason of optical clarity explained above in relation to the water bath 12, in such a case the sensor 200 is desirably arranged above the liquid level in the cuvette.

The patents and patent applications referred to herein are all hereby incorporated by reference herein in their entirities.

Although the present invention as described above is embodied in a clinical analyzer for biological samples, it will be understood that it is equally suited to other applications which involve the selective dispensing of tablets into containers. Thus, it may for example be employed in any chemical analyzer where tablets are dispensed into selected containers advanced past the tablet dispenser.

We claim:

1. A clinical analysis system for analyzing biological samples, including:

a plurality of processing stations, a strip of interconnected cuvettes having open mouths, means for advancing said strip of interconnected cuvettes in steps corresponding to the spacing between adjacent cuvettes past said processing stations to align said cuvettes successively with said processing stations in turn, and control means programmed to selectively activate said processing stations as said cuvettes are advanced therepast so that different cuvettes are processed differently from one another as they are advanced past said processing stations, one of said processing stations comprising:

a tablet dispensing means including a motor for driving the dispensing means to dispense a tablet, sensing means arranged below the mouth of a cuvette aligned with said tablet dispensing means to sense whether a tablet has entered the cuvette, and signal generating means operatively associated with said sensing means for generating a signal indicating the absence of a tablet, said control means being programmed to activate said tablet dispensing means selectively to dispense tablets only when selected ones of said cuvettes are aligned with said tablet dispensing means by said advancing means such that said tablet dispensing means is activated to dispense tablets into less than all of said cuvettes and said sensing means being activated only when said tablet dispensing means is activated, being activated for a predetermined time each time said motor is activated, whereby a signal indicating the absence of a tablet can only be generated when the motor of the tablet dispensing means is activated to cause the tablet dispensing means to dispense a tablet, said advancing means being operable to advance said cuvette strip independently of the operation of said tablet dispensing means whereby operation of said advancing means is not dependent upon the dispensing of a tablet by said tablet dispensing means, and said control means being responsive to a signal from said signal generating means to vary further operation of said processing stations in a predetermined manner from that programmed to occur in the absence of said signal.

2. A clinical analysis system according to claim 1 including means for dispensing at least a liquid into a cuvette to be aligned with the tablet dispensing means to define a liquid level at a predetermined height in said cuvette, said sensing means being arranged at a level below the mouth of said cuvette and above said liquid level when said cuvette is aligned with said tablet dispensing means.

3. A clinical analysis system according to claim 1 in which said sensing means includes two light sources.

4. A clinical analysis system according to claim 1 including one or both of audio and visual warning means for indicating the absence of a tablet to an operator.

* * * * *